United States Patent
Arenas et al.

(10) Patent No.: US 7,465,582 B1
(45) Date of Patent: Dec. 16, 2008

(54) NURR-1 INDUCTION OF A DOPAMINERGIC NEURONAL FATE IN A NEURAL STEM CELL OR NEURAL PROGENITOR CELL IN VITRO

(75) Inventors: Ernest Arenas, Stockholm (SE);
Thomas Perlmann, Sollentuna (SE);
Evan Y. Snyder, Boston, MA (US);
Joseph Wagner, West Chester, PA (US);
Peter Akerud, Stockholm (SE)

(73) Assignee: Neuro Therapeutics AB, Stockholm (SE)

( * ) Notice: Subject to any disclaimer, the term of this patent is extended or adjusted under 35 U.S.C. 154(b) by 0 days.

(21) Appl. No.: 09/980,913

(22) PCT Filed: Apr. 27, 2000

(86) PCT No.: PCT/EP00/03842

§ 371 (c)(1),
(2), (4) Date: May 21, 2002

(87) PCT Pub. No.: WO00/66713

PCT Pub. Date: Nov. 9, 2000

(51) Int. Cl.
*C12N 15/00* (2006.01)
(52) U.S. Cl. .................... 435/377; 435/375; 435/325
(58) Field of Classification Search .................. 435/6, 435/69.1, 320.1, 325, 375; 514/44; 536/23.1
See application file for complete search history.

(56) References Cited

U.S. PATENT DOCUMENTS

| | | | |
|---|---|---|---|
| 5,981,165 A | * | 11/1999 | Weiss et al. ............. 435/4 |
| 6,284,539 B1 | * | 9/2001 | Bowen et al. .......... 435/455 |
| 6,312,949 B1 | | 11/2001 | Sakurada et al. |
| 6,833,269 B2 | | 12/2004 | Carpenter |
| 2002/0114788 A1 | | 8/2002 | Isacson et al. |

FOREIGN PATENT DOCUMENTS

| | | |
|---|---|---|
| WO | WO 96 09543 A | 5/1996 |
| WO | WO 9615224 A | 5/1996 |
| WO | 00/58451 | 10/2000 |
| WO | 02/09733 | 2/2002 |

OTHER PUBLICATIONS

Verma, et al. Nature, Sep. 1997, vol. 389, pp. 239-242.*
Palu, et al. J. Biotechnology, 1999, vol. 68, pp. 1-13.*
Luo, et al. Nature Biotechnology, 2000, vol. 18, pp. 33-37.*
Fox, Jeffrey. ASM News, Feb. 2000, vol. 66, No. 2, pp. 1-3.*
Hsich, et al. Human Gene Therapy, Mar. 2002, vol. 13, pp. 579-604.*
Tenenbaum L, Chtarto A, Lehtonen E, Blum D, Baekelandt V, Velu T, Brotchi J, Levivier M. 2002. Neuroprotective gene therapy for Parkinson's disease. Curr Gene Ther. 2(4):451-83.*
Takeshima T, Shimoda K, Sauve Y Commissiong, JW. 1994 .Astrocyte dependent and independent phases of the development and survival of rat embryonic day 14 mesencephalic dopaminergic neurons in culture. Neuroscience 60(3):809-823.*
Gerlach M, Braak H, hartmann A, Jost WH , Odin P, Priller J, Schwarz J. 2002.Current state of stem cell research for the treatment of Parkinson's disease. J Neurol. Oct. 2002;249 Suppl 3:III/33-5.*
Song H, Stevens CF, Gage FH. Astroglia induce neurogenesis from adult neural stem cells.Nature. May 2, 2002;417(6884):39-44.*
E. Arenas et al., *Nurr1 overexpression enriches for neuronal phenotype in multipotent, neural stem-like cells*, Society for Neuroscience Abstracts, 28th Annual Meeting of the Society for Neuroscience, Part 2, Los Angeles, US , Nov. 7-12, 1998, vol. 24, 1998, p. 1531, Abstract 606.10.
D.M. Panchision et al., *An immortalized type-1 astrocyte of mesencephalic origin; source of a dopaminergic neurotrophic factor*. Journal of Molecular Neuroscience, vol. 11, No. 3, 1998, pp. 209-221.
T. Takeshima et al., *Astrocyte-dependent and -independent phases of the development and survival of rat embryonic day 14 mesencephalic, dopaminergic neurons in culture*. Neuroscience, vol. 60, No. 3, 1994, pp. 809-823.
A. Gritti et al., *Basic fibroblast growth factor supports the proliferation of epidermal growth factor-generated neuronal precusors cells of the adult mouse CNS*. Neuroscience letters, vol. 185, No. 3, 1995, pp. 151-154.
O. Saucedo-Cardenas et al., *Nurr1 is essential for the induction of the dopaminergic phenotype and the survival of ventral mesencephalic late dopaminergic precursor neurons*. PNAS USA, vol. 95, Mar. 1998, pp. 4013-4018.
J. Wagner et al., *Induction of a midbrain dopaminergic phenotype in Nurr1-overexpressing neural stem cells by type 1 astrocytes*. Nature Biotechnology, vol. 17, Jul. 1999, pp. 653-659.
K. Sakurada et al., *Nurr1, an orphan nuclear receptor ia a transcriptional activator of endogenous tyrosine hydroxylase in neural progenitor cells derived from the adult brain*. Development, vol. 126, Sep. 1999, pp. 4017-4026.
S. Denis-Donini et al., *Glial heterogeneity may define the three-dimensional shape of mouse mesencephalic dopaminergic neurones*. Nature, vol. 307, Feb. 1984, pp. 641-643.

(Continued)

*Primary Examiner*—Deborah Crouch
(74) *Attorney, Agent, or Firm*—Morrison & Foerster LLP

(57) ABSTRACT

The invention relates to the induction of the neuronal fate in neural stem cells or neural progenitor cells. The inventors have found that a neuronal fate in a neural stem cell or neural progenitor cell can be induced by expressing Nurr1 above basal levels within the cell. Nurr1 is a transcription factor of the thyroid hormone/retinoic acid nuclear receptor superfamily. It is shown herein that the expression of Nurr1 above basal levels in neural stem cells or neural progenitor cells increases the proportion of the cells which differentiate toward a neural fate. It has been found that in particular, dopaminergic neural stem cells or progenitor cells by a process including expression of Nurr1 above basal levels in the cells and contact of the cells with one or more factors supplied by or derived from Type I astrocytes of the ventral mesencephalon.

12 Claims, 3 Drawing Sheets

OTHER PUBLICATIONS

Haque NS, LeBlanc CJ, Isacson O. Differential dissection of the rat E16 ventral mesencephalon and survival and reinnervation of the 6-OHDA-lesioned striatum by a subset of aldehyde dehydrogenase-positive TH neurons. Cell Transplant. May-Jun. 1997;6(3):239-48.

Åkerud P., Canals J., Snyder E.Y. and Arenas E. (2001) Neuroprotection through delivery of GDNF by neural stem cells in a mouse model of Parkinson's disease. Journal of Neuroscience, 21:8108-8118.

Åkerud P., Holm P.C., Castelo-Branco G., Sousa K., Rodriguez FJ and Arenas E. (2002) Persephin-overexpressing neural stem cells regulate the function of nigrostriatal dopaminergic neurons and prevent their degeneration in a model of Parkinson's disease. Molecular and Cellular Neuroscience, 21: 205-222.

Freed CR, Leehey MA, Zawada M, Bjugstad K, Thompson L, Breeze RE. Do patients with Parkinson's disease benefit from embryonic dopamine cell transplantation? J Neurol. Oct. 2003;250 Suppl 3:III44-6.

Dunnett SB, Björklund A, Lindvall O. (2001) Cell therapy in Parkinson's disease—stop or go? Nat Rev Neurosci. 2001, 2(5):365-9.

Von Bohlen und Halbach OB, Schober A, Krieglstein K. Genes, proteins, and neurotoxins involved in Parkinson's disease. Prog Neurobiol. Jun. 2004;73(3):151-77.

Schwarz J. Rationale for dopamine agonist use as monotherapy in Parkinson's dissease. Curr Opin Neurol. Dec. 2003;16 Suppl 1:S27-33.

Gill SS, Patel NK, Hotton GR, O'Sullivan K, McCarter R, Bunnage M, Brooks DJ, Svendsen CN, Heywood P. Direct brain infusion of glial cell line-derived neurotrophic factor in Parkinson disease. Nat Med. May 2003;9(5):589-95.

Kordower JH, Emborg ME, Bloch J, Ma SY, Chu Y, Leventhal L, McBride J, Chen EY, Palfi S, Roitberg BZ, Brown WD, Holden JE, Pyzalski R, Taylor MD, Carvey P, Ling Z, Trono D, Hantraye P, Deglon N, Aebischer P (2000) Neurodegeneration prevented by lentiviral vector delivery of GDNF in promate models of Parkinson's disease. Science 290(5492): 767-773.

Bjorklund A, Dunnett SB, Brundin P, Stoessl AJ, Freed CR, Breeze RE, Levivier M, Peschanski M, Studer L, Barker R. Neural transplantation for the treatment of Parkinson's disease. Lancet Neurol. Jul. 2003;2(7):437-45.

Wagner J., Åkerud P., Castro D., Holm P C., Canals J M., Snyder E Y., Perlmann T. and Arenas E. (a999). Induction of a Midbrain Dopaminergic Phenotype in Nurr1-Overexpressing Neural Stem Cells. Nature Biotechnology, 17: 653-659.

Cochen V, Ribeiro MJ, Nguyen JP, Gurruchaga JM, Villafane G, Loc'h C, Defer G, Samson Y, Peschanski M, Hantraye P, Cesaro P, Remy P. Transplantation in Parkinson's disease: PET changes correlate with the amount of grafted tissue. Mov Disord. Aug. 2003;18(8):928-32.

Hagell P, Brundin P. Cell survival and clinical outcome following intrastriatal transplantation in Parkinson disease. J Neuropathol Exp Neurol. Aug. 2001;60(8):741-52.

Piccini P, Lindvall O, Bjorklund A, brundin P, Hagell P, Ceravolo R, Oertel W, Quinn N, Samuel M, Rehncrona S, Widner H, Brooks DJ. Related Articles, Links Abstract Delayed recovery of movement-related cortical function in Parkinson's disease after striatal dopaminergic grafts. Ann Neurol. Nov. 2000;48(5):689-95.

Kirik, D., et al., "Localized striatal delivery of GDNF as a treatment for Parkinson disease", Nature Neuroscience, vol. 7: p. 105-110, (2004).

* cited by examiner

NURR-1 INDUCTION OF A DOPAMINERGIC NEURONAL FATE IN A NEURAL STEM CELL OR NEURAL PROGENITOR CELL IN VITRO

FIELD OF THE INVENTION

The present invention relates to the induction of the neuronal fate in neural stem cells or neural progenitor cells. It relates to the induction of a specific neuronal phenotype, and particularly to the induction of a midbrain dopaminergic neuronal phenotype.

BACKGROUND OF THE INVENTION

Neural stem cells have the ability to differentiate into neurons, astrocytes and oligodendrocytes. Recent advances in neural stem cell biology have shown that such stem cells can be isolated, expanded, and used as source material for brain transplants (Snyder, E. Y. et al. Cell 68, 33-51 (1992); Rosenthal, A. Neuron 20, 169-172 (1998); Gage, F. H., et al. Ann. Rev. Neurosci. 18, 159-192 (1995); Weiss, S. et al. Trends Neurosci. 19, 387-393 (1996); Snyder, E. Y. et al. Clin. Neurosci. 3, 310-316 (1996); Martinez-Serrano, A. et al. Trends Neurosci. 20, 530-538 (1997); McKay, R. Science 276, 66-71 (1997); Studer, L. et al. Nature Neurosci. 1, 290-295 (1998)). However, although multiple studies demonstrate that implanted neural stem cells successfully engraft and assume legitimate neural phenotypes, when transplanted into the intact adult brain these cells seem biased toward astro- and oligodendroglial fates (Martínez-Serrano, A. et al. Trends Neurosci. 20, 530-538 (1997); McKay, R. Science 276, 66-71 (1997); Snyder, E. Y. et al. Proc. Natl. Acad. Sci. USA 94, 11663-11668 (1997)).

Most neurodegenerative diseases affect neuronal populations. Moreover, most of the damage occurs to a specific neurochemical phenotype. In human Parkinson's disease, for example, the major cell type lost is midbrain dopaminergic neurons. Functional replacement of specific neuronal populations through transplantation of neural tissue represents an attractive therapeutic strategy for treating neurodegenerative diseases (Rosenthal, A. Neuron 20, 169-172 (1998))

SUMMARY OF THE INVENTION

An ideal material for use in transplantation therapy is an expandable cell that could be instructed to assume a neuronal phenotype, particularly a specific neuronal phenotype, upon differentiation. This strategy would circumvent ethical and practical issues surrounding the use of human fetal tissue for transplantation. In particular, implanted embryonic cells are of limited viability and are often rejected. In addition, each fetus provides only a small number of cells.

Induction of a single and specific neuronal phenotype in multipotent neural stem or progenitor cells in vitro has proven elusive.

In a first aspect, the present invention provides a method of inducing a neuronal fate in a neural stem cell or neural progenitor cell, the method including expressing Nurr1 above basal levels within the cell.

Nurr1 (Law, et al., (1992) Mol Endocrinol 6, 2129-2135; Xing, et al., (1997) Mol Brain Res 47, 251-261; Castillo (1997) Genomics, 41, 250-257; GenBank nos. S53744, U72345, U86783) is a transcription factor of the thyroid hormone/retinoic acid nuclear receptor superfamily. The present disclosure shows that expression of Nurr1 above basal levels in neural stem cells or neural progenitor cells increases the proportion of the cells which differentiate toward a neuronal fate. The induction of a neuronal fate may be carried out in vitro or in vivo. The ability to induce differentiation of neural stem or progenitor cells toward the neuronal fate prior to, or following transplantation ameliorates the biasing of transplanted stem cells to the astro- and oligodendroglial fates.

By "neural stem cell" is meant any cell type that can divide more than once and can give rise to cells that exhibit the most primitive type of phenotypes for neurons, astrocytes and oligodendrocytes. The neural stem cell may express one or more of the following markers: Nestin; the p75 neurotrophin receptor; Notch1. By "neural progenitor cell" is meant a multipotent daughter of a neural stem cell, which daughter is restricted in its potential fates and/or has a reduced proliferative potential compared to the neural stem cell. In preferred embodiments, the neural stem or progenitor cell does not express tyrosine hydroxylase either spontaneously or upon deprivation of mitogens (e.g. bFGF, EGF or serum).

The neural stem cell or neural progenitor cell may be obtained or derived from any region of the nervous system, e.g. from the cerebellum, the ventricular zone, the sub-ventricular zone or the hippocampus. It may be obtained or derived from a vertebrate organism, e.g. from a mammal, which may be human or non-human, such as rabbit, guinea pig, rat, mouse or other rodent, cat, dog, pig, sheep, goat, cattle, horse, or primate, or from a bird, such as a chicken.

The neuronal fate to which the neural stem or progenitor cell is induced may exhibit a primitive neuronal phenotype. It may be a multipotent cell which is capable of giving rise to a plurality of distinct neuronal phenotypes. It may lack markers associated with specific neuronal fates, e.g. tyrosine hydroxylase.

In a method of inducing a neuronal fate according to the present invention wherein a plurality of neural stem cells and/or progenitor cells express Nurr1 above basal levels, a majority of the stem or progenitor cells may be induced to adopt a neuronal fate. In preferred embodiments, more than 60%, more than 70%, more than 80%, more than 90% of the stem and/or progenitor cells may be induced to a neuronal fate.

By "expressing Nurr1 above basal levels within the cell" is meant expressing Nurr1 at levels greater than that at which it is expressed in the (unmodified) cell in vivo under non-pathological conditions. Expression above basal levels includes pharmacological and artificial upregulation and over-expression.

Expression of Nurr1 above basal levels may be achieved by any method known to those skilled in the art. By way of example, expression above basal levels may be induced by modulating the regulation of native genomic Nurr1. This may be done by increasing transcription and/or translation of Nurr1, e.g. by contacting the cell with fibroblast growth factor 8 (FGF8), which upregulates transcription of Nurr1 (Rosenthal, A., (1998) Cell, 93(5), 755-766), and/or by introducing heterologous regulatory sequences into or adjacent the native regulatory region of Nurr1, and/or by replacing the native regulatory region of Nurr1 with such heterologous regulatory sequences, e.g. by homologous recombination, and/or by disrupting or downregulating molecules that negatively regulate, block or downregulate transcription, translation or the function of Nurr1, e.g. Nurr2 (Ohkura, et al., (1999) Biochim Biophys Acta 14444: 69-79).

Transcription may be increased by providing the neural stem or progenitor cell with increased levels of a transcriptional activator, e.g. by contacting the cell with such an activator or by transformation of the cell with nucleic acid encoding the activator. Alternatively, transcription may be increased by transforming the cell with antisense nucleic acid to a transcriptional inhibitor of Nurr1.

Accordingly, a method of the present invention of inducing a neuronal fate in a neural stem or progenitor cell, may include contacting the cell with FGF8.

As an alternative or addition to increasing transcription and/or translation of endogenous Nurr1, expression of Nurr1 above basal levels may be caused by introduction of one or more extra copies of Nurr1 into the neural stem or progenitor cell.

Accordingly, in a further aspect, the present invention provides a method of inducing a neuronal fate in a neural stem cell or neural progenitor cell, the method including transforming the cell with Nurr1. Transformation of the neural stem or progenitor cell may be carried out in vitro or in vivo. The neuronal fate to which the neural stem or progenitor cell is induced may be of the type discussed herein, e.g. it may exhibit a primitive neuronal phenotype and may lack markers associated with specific neuronal fates. The invention further provides a neural stem cell or neural progenitor cell transformed with Nurr1.

Transformed Nurr1 may be contained on an extra-genomic vector or it may be incorporated, preferably stably, into the genome. It may be operably-linked to a promoter which drives its expression above basal levels in neural stem or progenitor cells, as is discussed in more detail below.

"Operably linked" means joined as part of the same nucleic acid molecule, suitably positioned and oriented for transcription to be initiated from the promoter.

Methods of introducing genes into cells are well known to those skilled in the art. Vectors may be used to introduce Nurr1 into neural stem or progenitor cells, whether or not the Nurr1 remains on the vector or is incorporated into the genome. Suitable vectors can be chosen or constructed, containing appropriate regulatory sequences, including promoter sequences, terminator fragments, polyadenylation sequences, enhancer sequences. Vectors may contain marker genes and other sequences as appropriate. The regulatory sequences may drive expression of Nurr1 within the neural stem or progenitor cells. For example, the vector may be an extra-genomic expression vector, or the regulatory sequences may be incorporated into the genome with Nurr1. Vectors may be plasmids or viral.

Nurr1 may be placed under the control of an externally inducible gene promoter to place it under the control of the user. The term "inducible" as applied to a promoter is well understood by those skilled in the art. In essence, expression under the control of an inducible promoter is "switched on" or increased in response to an applied stimulus. The nature of the stimulus varies between promoters. Some inducible promoters cause little or undetectable levels of expression (or no expression) in the absence of the appropriate stimulus. Whatever the level of expression is in the absence of the stimulus, expression from any inducible promoter is increased in the presence of the correct stimulus. An example of an inducible promoter is the Tetracyclin ON/OFF system (Gossen, et al., (1995) Science, 268, 1766-1769) in which gene expression is regulated by tetracyclin analogs.

For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Ausubel et al. eds., John Wiley & Sons, 1992.

Marker genes such as antibiotic resistance or sensitivity genes may be used in identifying clones containing nucleic acid of interest, as is well known in the art. Clones may also be identified or further investigated by binding studies, e.g. by Southern blot hybridisation.

Nucleic acid including Nurr1 may be integrated into the genome of the host neural stem cell or neural progenitor cell. Integration may be promoted by including in the transformed nucleic acid sequences which promote recombination with the genome, in accordance with standard techniques. The integrated nucleic acid may include regulatory sequences able to drive expression of the Nurr1 gene in neural stem or progenitor cells. The nucleic acid may include sequences which direct its integration to a site in the genome where the Nurr1 coding sequence will fall under the control of regulatory elements able to drive and/or control its expression within the neural stem or progenitor cell. The integrated nucleic acid may be derived from a vector used to transform Nurr1 into the neural stem or progenitor cells, as discussed herein.

The introduction of nucleic acid comprising Nurr1, whether that nucleic acid is linear, branched or circular, may be generally referred to without limitation as "transformation". It may employ any available technique. Suitable techniques may include calcium phosphate transfection, DEAE-Dextran, electroporation, mechanical techniques such as microinjection, direct DNA uptake, receptor mediated DNA transfer, transduction using retrovirus or other virus and liposome-mediated transfection. When introducing a chosen gene construct into a cell, certain considerations must be taken into account, well known to those skilled in the art. It will be apparent to the skilled person that the particular choice of method of transformation to introduce Nurr1 into neural stem or progenitor cells is not essential to or a limitation of the invention.

Suitable vectors and techniques for in vivo transformation of neural stem or progenitor cells with Nurr1 are well known to those skilled in the art. Suitable vectors include adenovirus, papovavirus, vaccinia virus, herpes virus and retroviruses. Disabled virus vectors may be produced in helper cell lines in which genes required for production of infectious viral particles are expressed. Suitable helper cell lines are well known to those skilled in the art. By way of example, see: Fallaux, F. J., et al., (1996) Hum Gene Ther 7(2), 215-222; Willenbrink, W., et al., (1994) J Virol 68(12) 8413-8417; Cosset, F. L., et al., (1993) Virology 193(1), 385-395; Highkin, M. K., et al., (1991) Poult Sci 70(4), 970-981; Dougherty, J. P., et al., (1989) J Virol 63(7), 3209-3212; Salmons, B., et al., (1989) Biochem Biophys Res Commun 159(3), 1191-1198; Sorge, J., et al., (1984) Mol Cell Biol 4(9), 1730-1737; Wang, S., et al., (1997) Gene Ther 4(11), 1132-1141; Moore, K. W., et al., (1990) Science 248(4960), 1230-1234; Reiss, C. S., et al., (1987) J Immunol 139(3), 711-714. Helper cell lines are generally missing a sequence which is recognised by the mechanism which packages the viral genome. They produce virions which contain no nucleic acid. A viral vector which contains an intact packaging signal along with the gene or other sequence to be delivered (Nurr1) is packaged in the helper cells into infectious virion particles, which may then be used for gene delivery to neural stem or progenitor cells.

In a further aspect, the present invention provides a method of inducing a specific neuronal fate in a neural stem or progenitor cell, wherein the stem cell or progenitor cell expresses Nurr1 above basal levels, the method including contacting the cells with one or more factors supplied by or derived from a Type 1 astrocyte. The factor or factors may be provided by co-culturing the neural stem cell or neural progenitor cell with a Type 1 astrocyte. The method may occur in vitro or in vivo. The neural stem or progenitor cells expressing Nurr1 above basal levels may be produced by transformation of the cells with Nurr1.

The factor or factors may be supplied by or derived from an immortalized astrocyte. The factor or factors may be supplied by or derived from an astrocyte cell line, e.g. an astrocyte mesencephalic cell line. Cell lines provide a homogenous cell population.

The present disclosure provides the first evidence that Type 1 astrocytes are involved in the determination of specific neuronal fates. The data presented herein suggests that astrocytes from distinct brain regions may be used as a source of signals required for the induction of regionally appropriate neuronal phenotypes in multiple brain structures.

Important aspects of the present invention are based on the finding that dopaminergic neurons can be generated from multipotent neural stem cells or progenitor cells in vitro by a process including expression of Nurr1 above basal levels in the cells and contact of the cells with one or more factors supplied by or derived from Type 1 astrocytes of the ventral mesencephalon.

Accordingly, the specific neuronal fate is preferably a dopaminergic fate, and the Type 1 astrocyte is preferably a Type 1 astrocyte of the ventral mesencephalon.

The present invention allows for generation of large numbers of dopaminergic neurons. These dopaminergic neurons may be used as source material to replace cells which are damaged or lost in Parkinson's disease.

Preferably, the neural stem or progenitor cell expressing Nurr1 above basal levels is mitotic when it is contacted with the one or more factors supplied by or derived from the Type 1 astrocyte.

In inducing a dopaminergic fate in a neural stem or progenitor cell, the cell may additionally be contacted with one or more agents selected from: basic fibroblast growth factor (bFGF) epidermal growth factor (EGF); and an activator of the retinoid X receptor (RXR), e.g. the synthetic retinoid analog SR11237, (Gendimenico, C. J., et al., (1994) J Invest Dermatol 102 (5), 676-80), or 9-cis retinol. Treating a co-culture of neural stem and/or progenitor cells expressing Nurr1 above basal levels and Type 1 astrocytes with one or more of these agents may be used to increase the proportion of the stem and/or progenitor cells which adopt a dopaminergic fate, as demonstrated experimentally below. The method of inducing a dopaminergic fate in accordance with the present invention may include contacting the neural stem or progenitor cell with a member of the FGF family of growth factors, e.g. FGF4, FGF8.

Advantageously, the cells may be contacted with two or more of the above agents. The inventors have unexpectedly found that the beneficial effects of bFGF or EGF and SR11237 are additive at saturating doses. This finding suggests that these agents may act through different mechanisms.

The method of inducing a dopaminergic phenotype may include pretreating the neural stem cell or neural progenitor cell with bFGF and/or EGF prior to contacting it with the one or more factors supplied by or derived from Type 1 astrocytes of the ventral mesencephalon, e.g. prior to co-culturing it with a Type 1 astrocyte of the ventral mesencephalon.

The optional pretreatment step arises from two further unexpected findings of the inventors: (i) that neural stem cell lines expressing Nurr1 above basal levels and showing high proliferation demonstrate enhanced induction to dopaminergic fate when co-cultured with Type 1 astrocytes of the ventral mesencephalon; and (ii) that after treatment with bFGF or EGF in serum-free medium (SFM), the baseline proliferation of most stem cell lines expressing Nurr1 above basal levels remained elevated after passage into SFM alone. The method of inducing a dopaminergic phenotype may include pretreating a neural stem cell or progenitor cell with a member of the FGF family of growth factors, e.g. FGF4, FGF8.

A method according to the invention in which a neuronal fate is induced in a multipotent neural stem or progenitor cell may include detecting a marker for the neuronal fate. β-tubulin III (TuJ1) is one marker of the neuronal fate (Menezes, J. R., et al., (1994) J Neurosci 14(9), 5399-5416). If a particular neuronal phenotype is induced, the marker should be specific for that phenotype. For the dopaminergic fate, expression of tyrosine hydroxylase (TH) and/or release of dopamine and/or DOPAC may be detected e.g. by immunoreactivity (Cooper, J. R., et al., The Biochemical Basis of Neuropharmacology, 7th Edition, (1996) Oxford University Press). The absence of Dopamine β hydroxylase (in the presence of TH/dopamine/DOPAC) is also indicative of dopaminergic fate.

Detection of a marker may be carried out according to any method known to those skilled in the art. The detection method may employ a specific binding member capable of binding to a nucleic acid sequence encoding the marker, the specific-binding member comprising a nucleic acid probe hybridisable with the sequence, or an immunoglobulin/antibody domain with specificity for the nucleic acid sequence or the polypeptide encoded by it, the specific binding member being labelled so that binding of the specific binding member to the sequence or polypeptide is detectable. A "specific binding member" has a particular specificity for the marker and in normal conditions binds to the marker in preference to other species. Alternatively, where the marker is a specific mRNA, it may be detected by binding to specific oligonucleotide primers and amplification in e.g. the polymerase chain reaction.

Nucleic acid probes and primers may hybridize with the marker under stringent conditions. Suitable conditions include, e.g. for detection of marker sequences that are about 80-90% identical, hybridization overnight at 42° C. in 0.25M $Na_2HPO_4$, pH 7.2, 6.5% SDS, 10% dextran sulfate and a final wash at 55° C. in 0.1×SSC, 0.1% SDS. For detection of marker sequences that are greater than about 90% identical, suitable conditions include hybridization overnight at 65° C. in 0.25M $Na_2HPO_4$, pH 7.2, 6.5% SDS, 10% dextran sulfate and a final wash at 60° C. in 0.1×SSC, 0.1% SDS.

In a further aspect, the present invention provides a neuron produced in accordance with any one of the methods disclosed herein. The neuron may have a primitive neuronal phenotype. It may be capable of giving rise to a plurality of distinct neuronal phenotypes. The neuron may have a particular neuronal phenotype, the phenotype being influenced by the type of astrocyte from which the factor or factors which contacted the neural stem or progenitor cell expressing Nurr1 above basal levels were supplied or derived, or by the type of astrocyte with which the stem or progenitor cell was co-cultured. In preferred embodiments, the neuron has a dopaminergic phenotype.

The neuron may contain nucleic acid encoding a molecule with neuroprotective or neuroregenerative properties operably linked to a promoter which is capable of driving expression of the molecule in the neuron. The promoter may be an inducible promoter, e.g. the TetON chimeric promoter, so that any damaging over-expression may be prevented. The promoter may be associated with a specific neuronal phenotype, e.g. the TH promoter.

The encoded molecule may be such that its expression renders the neuron independent of its environment, i.e. such that its survival is not dependent on the presence of one or more factors or conditions in e.g. the neural environment into which it is to be implanted. By way of example, the neuron may contain nucleic acid encoding one or more of the neuroprotective or neuroregenerative molecules described below operably linked to a promoter which is capable of driving expression of the molecule in the neuron.

In addition or alternatively, expression of the encoded molecule may function in neuroprotection or neuroregeneration of the cellular environment surrounding that neuron. In this way, the neuron may be used in a combined cell and gene therapy approach to deliver molecules with neuroprotective and neuroregenerative properties.

Examples of molecules with neuroprotective and neuroregenerative properties include:

(i) neurotropic factors able to compensate for and prevent neurodegeneration. One example is glial derived neurotropic growth factor (GDNF) which is a potent neural survival factor, promotes sprouting from dopaminergic neurons and increases tyrosine hydroxylase expression (Tomac, et al., (1995) Nature, 373, 335-339; Arenas, et al., (1995) Neuron, 15, 1465-1473) By enhancing axonal elongation GDNF, GDNF may increase the ability of the neurons to inervate their local environment. Other neurotropic molecules of the GDNF family include Neurturin, Persephin and Artemin. Neurotropic molecules of the neurotropin family include nerve growth factor (NGF), brain derived neurotropic factor (BDNF), and neurotropin-3, -4/5 and -6.

(ii) antiapoptotic molecules. Bcl2 which plays a central role in cell death. Over-expression of Bcl2 protects neurons from naturally occurring cell death and ischemia (Martinou, et al., (1994) Neuron, 1017-1030). Another antiapoptotic molecule is BclX-L.

(iii) axon regenerating and/or elongating and/or guiding molecules which assist the neuron in innervating and forming connections with its environment, e.g. ephrins. Ephrins define a class of membrane-bound ligands capable of activating tyrosine kinase receptors. Ephrins have been implicated in neural development (Irving, et al., (1996) Dev. Biol., 173, 26-38; Krull, et al., (1997) Curr. Biol. 7, 571-580; Frisen, et al., (1998) Neuron, 20, 235-243; Gao, et al., (1996) PNAS, 93, 11161-11166; Torres, et al., (1998) Neuron, 21, 1453-1463; Winslow, et al., (1995) Neuron, 14, 973-981; Yue, et al., (1999) J Neurosci 19(6), 2090-2101.

(iv) differentiation molecules, e.g. the homeobox domain protein Ptx3 (Smidt, M. P., et al., (1997) Proc Natl Acad Sci USA, 94(24), 13305-13310).

A neuron in accordance with or for use in the present invention may be substantially free from one or more other cell types, e.g. from neural stem or progenitor cells. Neurons may be separated from neural stem or progenitor cells using any technique known to those skilled in the art. By way of example, antibodies against extracellular regions of molecules found on neural stem or progenitor cells but not on neurons may be employed. Such molecules include Notch 1 and the glial cell line derived neurotrophic factor receptor GFR α2. Stem cells bound to antibodies may be lysed by exposure to complement, or separated by, e.g. magnetic sorting (Johansson, et al., (1999) Cell, 96, 25-34). If antibodies which are xenogeneic to the intended recipient of the neurons are used, then any e.g. neural stem or progentior cells which escape such a cell sorting procedure are labelled with xenogeneic antibodies and are prime targets for the recipient's immune system.

The present invention extends in various aspects not only to a neuron produced in accordance with any one of the methods disclosed herein, but also a pharmaceutical composition, medicament, drug or other composition comprising such a neuron, use of such a neuron or composition in a method of medical treatment, a method comprising administration of such a neuron or composition to a patient, e.g. for treatment (which may include preventative treatment) of Parkinson's disease or other (e.g. neurodegenerative) diseases, use of such a neuron in the manufacture of a composition for administration, e.g. for treatment of Parkinson's disease or other (e.g. neurodegenerative diseases), and a method of making a pharmaceutical composition comprising admixing such a neuron with a pharmaceutically acceptable excipient, vehicle or carrier, and optionally one or more other ingredients, e.g. a neuroprotective molecule, a neuroregenerative molecule, a retinoid, growth factor, astrocyte, anti-apoptotic factor, or factor that regulates gene expression in neural stem or progenitor cells or in the host brain. Such optional ingredients may render the neuron independent of its environment, i.e. such that its survival is not dependent on the presence of one or more factors or conditions in its environment. By way of example, the method of making a pharmaceutical composition may include admixing the neuron with one or more factors found in the developing ventral mesencephalon. The neuron may be admixed with GDNF and/or neurturin (NTN).

The present invention provides a composition containing a neuron produced in accordance with the invention, and one or more additional components. Pharmaceutical compositions according to the present invention, and for use in accordance with the present invention, may comprise, in addition to the neuron, a pharmaceutically acceptable excipient, carrier, buffer, preservative, stabiliser, anti-oxidant or other material well known to those skilled in the art. Such materials should be non-toxic and should not interfere with the activity of the neuron. The precise nature of the carrier or other material will depend on the route of administration. The composition may include one or more of a neuroprotective molecule, a neuroregenerative molecule, a retinoid, growth factor, astrocyte, or factor that regulates gene expression in neural stem or progenitor cells. Such substances may render the neuron independent of its environment as discussed above. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

The composition may be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride, Ringer's Injection, or Lactated Ringer's Injection. A composition may be prepared using artificial cerebrospinal fluid.

The present invention extends to the use of a neuron produced in accordance with the invention in a method of medical treatment, particularly the treatment of a medical condition associated with damage to, the loss of, or a disorder in, neuronal cells. Moreover, the invention may provide the use of a neuron of a specific phenotype in the treatment of a condition, disease or disorder which is associated with damage to, or the loss of neurons of that phenotype. More particularly, the invention provides the use of a dopaminergic neuron in the treatment of human Parkinson's disease. While the invention particularly relates to materials and methods for treatment of neurodegenerative diseases (e.g. Parkinson's disease), it is not limited thereto. By way of example, the invention extends to the treatment of damage to the spinal cord and/or cerebral cortex.

In methods of treatment in which the administered neuron is a pluripotent cell that is capable of giving rise to two or more distinct neuronal phenotypes, the neuron or composition may be introduced into a region containing astrocytes which direct the differentiation of the neuron to a desired specific neuronal fate. The neuron or composition may for example be injected into the ventral mesencephalon where it may interact with Type 1 astrocytes and be induced to adopt a dopaminergic phenotype. Alternatively or in addition, an implanted composition may contain a pluripotent neuron in combination with one or more factors which direct its development toward a specific neuronal fate as discussed above, e.g. with a Type 1 astrocyte.

Neurons may be implanted into a patient by any technique known in the art (e.g. Lindvall, O., (1998) Mov. Disord. 13, Suppl. 1: 83-7; Freed, C. R., et al., (1997) Cell Transplant, 6, 201-202; Kordower, et al., (1995) New England Journal of Medicine, 332, 1118-1124; Freed, C. R., (1992) New England Journal of Medicine, 327, 1549-1555).

Administration of a composition in accordance with the present invention is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors.

A composition may be administered alone or in combination with other treatments, either simultaneously or sequentially dependent upon the condition to be treated.

The methods provided herein for inducing a neuronal fate in neural stem or progenitor cells may be carried out using neural stem cell lines or neural progenitor cell lines as a source material. In this way there is virtually no limitation on the number of neurons which may be produced.

In order to ameliorate possible disadvantages associated with immunological rejection of transplanted cells, neural stem or progenitor cells may be isolated from a patient and induced to the desired phenotype. Advantageously, isolated neural stem or progenitor cells may be used to establish stem cell or progenitor cell lines so that large numbers of immunocompatible neuronal cells may be produced. A further option is to establish a bank of cells covering a range of immunological compatibilities from which an appropriate choice can be made for an individual patient. Neural stem or progenitor cells derived from one individual may be altered to ameliorate rejection when they or their progeny are introduced into a second individual. By way of example, one or more MHC alleles in a donor cell may be replaced with those of a recipient, e.g. by homologous recombination.

If neural stem or progenitor cells derived from a cell line carrying an immortalizing oncogene are used for implantation into a patient, the oncogene may be removed using the CRE-loxP system prior to implantation of the cells into a patient (Westerman, K. A. et al Proc. Natl. Acad. Sci. USA 93, 8971 (1996)). An immortalizing oncogene which is inactive at the body temperature of the patient may be used.

In a further aspect the present invention extends to the use of a neuron produced in accordance with the invention in a method of screening for an agent for use in the treatment of a neurodegenerative disease. The neuron may be a dopaminergic neuron. The neurodegenerative disease may be Parkinson's disease. The agent may be a neuroprotective and/or neuroregenerative molecule. The method may be carried out in vitro.

The method may include:

(i) treating a neuron of the invention with a toxin for said neuron;

(ii) separating the neuron from the toxin;

(iii) bringing the treated neuron into contact with a test agent or test agents;

(iv) determining the ability of the neuron to recover from the toxin;

(v) comparing said ability of the neuron to recover from the toxin with the ability of the or an identical neuron to recover from the toxin in the absence of contact with the test agent(s).

The method may include:

(i) treating a neuron of the invention with a toxin for the neuron in the presence of a test agent or test agents;

(ii) determining the ability of the neuron to tolerate the toxin;

(iii) comparing said ability of the neuron to tolerate the toxin with the ability of the or an identical neuron to tolerate the toxin in the absence of contact with the test agent(s).

The toxin may be 6-hydroxydopamine, 5,7-dihydroxytryptamine or 1-methyl-4-phenyl-1,2,3,6-tetrahydropyridine (MPTP). The ability of the neuron to recover from or tolerate the toxin may be determined by any method known to those skilled in the art, for example by monitoring cell viability, (e.g. by cell counting, e.g. by the TUNEL technique), by monitoring morphology, (e.g. sprouting, axonal elongation and/or branching), and/or by monitoring biochemistry, (e.g. TH activity, e.g. neurotransmitter uptake/release/content)

Neural stem or progenitor cells which may be used in the present invention include C17.2 (Snyder, E. Y. et al. Cell 68, 33-51 (1992)) and the H6 human cell line (Flax et al. Nature Biotech 16 (1998)). Further examples are listed in (Gage, F. H. et al. Ann. Rev. Neurosci. 18, 159-192 (1995)).

While the present discussion has been made with reference to neural stem cells or neural progenitor cells, the methods provided herein may be applied to the induction of neuronal fates in other stem/progenitor cells. Examples of such cells include stem cells associated with non-neural systems. The methods may be applied to hematopoietic stem cells and/or proliferative cells from the epidermis. Hematopoietic cells may be collected from blood or bone biopsy. Epithelial cells may be collected by skin biopsy or by scraping e.g. the oral mucosa. Since a neuronal phenotype is not a physiological in vivo fate of these stem/progenitor cells, the inductive process may be referred to as trans-differentiation, or desdifferentiation and neural redifferentiation. A method of inducing such cells to a neuronal fate may include the use of antisense regulators to genes associated with non-neuronal phenotypes, i.e. to suppress and/or reverse the differentiation of these cells toward non-neuronal fates.

The methods of the present invention may be applied to stem cells located before neural stem cells in the developmental pathway. They may be applied to stem cells which are capable of giving rise to two or more daughter stem cells associated with different developmental systems. Examples of daughter stem cells are hematopoietic stem cells, proliferative cells from the epidermis, and neural stem cells.

As discussed above, the present disclosure demonstrates that dopaminergic neurons can be generated from multipotent neural stem or progenitor cells by a process requiring expression of Nurr1 above basal levels in combination with one or more factors supplied by or derived from Type 1 astrocytes of the ventral mesencephalon. The one or more factors are soluble and secreted, as determined by a capacity to pass through a microporous insert. The factor or factors also appear to be labile.

In various further aspects the present invention is concerned with provision of assays and methods of screening for a factor or factors which induce a dopaminergic fate in a neural stem or progenitor cell expressing Nurr1 above basal levels, and with a factor or factors identified thereby.

The invention provides a method of screening for a factor or factors able, either alone or in combination, to induce a dopaminergic fate in a neural stem or progenitor cell expressing Nurr1 above basal levels. A further aspect of the present invention provides the use of a neural stem or progenitor cell expressing Nurr1 above basal levels in screening or searching for and/or obtaining/identifying a factor or factors which induce(s) a dopaminergic fate in such a stem or progenitor cell.

A method of screening may include:
(a) bringing a test substance into contact with a neural stem or progenitor cell expressing Nurr1 above basal levels, which contact may result in interaction between the test substance and the neural stem or progenitor cell; and
(b) determining interaction between the test substance and the stem or progenitor cell.

A method of screening may include bringing a test substance into contact with a membrane fraction derived from a neural stem or progenitor cell expressing Nurr1 above basal levels and determining interaction between the test substance and the membrane fraction. The preparation of membrane fractions is well within the capabilities of those skilled in the art.

Binding or interaction may be determined by any number of techniques known in the art, qualitative or quantitative. Interaction between the test substance and the stem or progenitor cell may be studied by labeling either one with a detectable label and bringing it into contact with the other which may have been immobilised on a solid support, e.g. by using an antibody bound to a solid support, or via other technologies which are known per se.

A screening method may include culturing a neural stem or progenitor cell in the presence of a test substance or test substances and analyzing the cell for differentiation to a dopaminergic phenotype, e.g. by detecting a marker of the dopaminergic phenotype as discussed herein. Tyrosine hydroxylase (TH) is one marker of the dopaminergic phenotype.

Any of the substances screened in accordance with by the present invention may be a natural or synthetic chemical compound.

A screening method may include comparing Type 1 astrocytes of the ventral mesencephalon with neural cells (e.g. astrocytes) which are unable to induce a dopaminergic fate in neural stem or progenitor cells expressing Nurr1 above basal levels. The comparison may for example be between Type 1 astrocytes of the ventral mesencephalon and Type 1 astrocytes from other neural locations.

A screening method involving astrocytes may employ immortalized astrocytes. It may involve astrocyte cell lines, e.g. astrocyte mesencephalic cell lines. Such cell lines provide a homogenous cell population.

A screening method may employ any known method for analyzing a phenotypic difference between cells and may be at the DNA, mRNA, cDNA or polypeptide level. Differential screening and gene screening are two such techniques. A substance identified by any of the methods of screening described herein may be used as a test substance in any of the other screening methods described herein.

A screening method may employ a nucleic expression array, e.g. a mouse cDNA expression array. In this approach, an array of different nucleic acid molecules is arranged on a filter, e.g. by cross-linking the nucleic acid to the filter. A test solution or extract is obtained and the nucleic acid within it is labeled, e.g. by fluorescence. The solution or extract is then applied to the filter. Hybridisation of the test nucleic acid to nucleic acid on the filter is determined and compared to the hybridisation achieved with a control solution. A difference between the hybridisation obtained with the test and control samples is indicative of a different nucleic acid content. For further information on nucleic acid arrays, see www.clontech.com.

A screening method may include comparing C17.2 parental cells with C17.2 cells which express Nurr1 above basal levels, e.g. to identify target genes of Nurr1 and/or the receptor(s) for the factor or factors which are supplied by or derived from Type 1 astrocytes of the ventral mesencephalon and which induce a dopaminergic fate in neural stem or progenitor cells expressing Nurr1 above basal levels. Once the target gene(s) and/or receptor(s) have been identified they may be isolated and/or purified and/or cloned and used in methods of screening for the factor or factors themselves, e.g. by affinity chromatography.

A screening method may include purifying and/or isolating a substance or substances from a mixture. The method may include determining the ability of one or more fractions of the mixture to interact with a neural stem cell or neural progenitor cell expressing Nurr1 above basal levels, e.g. the ability to bind to and/or induce a dopaminergic fate in such a neural stem or progenitor cell. The purifying and/or isolating may employ any method known to those skilled in the art.

A screening method may employ an inducible promoter operably linked to nucleic acid encoding a test substance. Such a construct is incorporated into a host cell and one or more properties of that cell under the permissive and non-permissive conditions of the promoter are determined and compared. The property determined may be the ability of the host cell to induce a dopaminergic phenotype in a co-cultured neural stem or progenitor cell expressing Nurr1 above basal levels. A difference in that ability of the host cell between the permissive and non-permissive conditions indicates that the test substance may be able, either alone or in combination, to induce a dopaminergic fate in a neural stem or progenitor cell expressing Nurr1 above basal levels.

The precise format of any of the screening methods of the present invention may be varied by those of skill in the art using routine skill and knowledge.

A factor or factors identified by any one of the methods provided by the invention may be isolated and/or purified and/or further investigated. It may be manufactured.

In various further aspects, the invention further provides a factor identified by any one of the methods disclosed herein, a pharmaceutical composition, medicament, drug or other composition comprising such a factor (which composition may include a neural stem or progenitor cell expressing Nurr1 above basal levels), use of such a factor to induce neural stem or progenitor cells expressing Nurr1 above basal levels to adopt a dopaminergic phenotype, use of such a factor or composition in a method of medical treatment, a method comprising administration of such a factor or composition to a patient, e.g. for treatment (which may include preventative treatment) of a medical condition associated with damage to, loss of, or a disorder in dopaminergic neurons, e.g. for treatment of Parkinson's disease or another neurodegenerative disease, use of such a factor in the manufacture of a composition, medicament or drug for administration, e.g. for treatment of Parkinson's disease or other (e.g. neurodegenerative diseases), and a method of making a pharmaceutical composition comprising admixing such a factor with a pharmaceutically acceptable excipient, vehicle or carrier, and optionally other ingredients.

In a related aspect, the present invention provides a method of screening for a substance which modulates the ability of Type 1 astrocytes of the ventral mesencephalon (or of a factor or factors identified by a screening method provided by the invention) to induce a dopaminergic fate in neural stem or progenitor cells expressing Nurr1 above basal levels.

Such a method may include one or more of:

(i) co-culturing Type 1 astrocytes with neural stem or progenitor cells which express Nurr1 above basal levels in the presence of one or more test substances;

(ii) bringing neural stem or progenitor cells which express Nurr1 above basal levels into contact with one or more factors identified by a screening method provided by the invention as being able to induce a dopaminergic phenotype in such cells, said contact occurring in the presence of one or more test substances;

(iii) analysing the proportion of stem or progenitor cells which adopt a dopaminergic fate;

(iv) comparing the proportion of stem or progenitor cells which adopt a dopaminergic fate with the number of stem or progenitor cells which adopt a dopaminergic fate in comparable reaction medium and conditions in the absence of the test substance(s). A difference in the proportion of dopaminergic neurons between the treated and untreated co-cultures is indicative of a modulating effect of the relevant test substance(s)

Such a method of screening may include:

(i) co-culturing Type 1 astrocytes with neural stem or progenitor cells which express Nurr1 above basal levels in the presence of one or more test substances;

(ii) analysing the proportion of stem or progenitor cells which adopt a dopaminergic fate;

(iii) comparing the proportion of stem or progenitor cells which adopt a dopaminergic fate with the number of stem or progenitor cells which adopt a dopaminergic fate in comparable reaction medium and conditions in the absence of the test substance(s).

Such a method may include:

(i) bringing neural stem or progenitor cells which express Nurr1 above basal levels into contact with one or more factors identified by a screening method provided by the invention as being able to induce a dopaminergic phenotype in such cells, said contact occurring in the presence of one or more test substances;

(ii) analysing the proportion of stem or progenitor cells which adopt a dopaminergic fate;

(iii) comparing the proportion of stem or progenitor cells which adopt a dopaminergic fate with the number of stem or progenitor cells which adopt a dopaminergic fate in comparable reaction medium and conditions in the absence of the test substance(s).

Following identification of a substance which modulates inductive activity, the substance may be investigated further. It may be manufactured and/or used in the preparation, i.e. manufacture or formulation, of a composition such as a medicament, pharmaceutical composition or drug. Any of substance tested for its modulating activity may be a natural or synthetic chemical compound.

Aspects and embodiments of the present invention will now be illustrated, by way of example, with reference to the accompanying figures. Further aspects and embodiments will be apparent to those skilled in the art. All documents mentioned in this specification are incorporated herein by reference.

BRIEF DESCRIPTION OF THE FIGURES

FIG. 1a shows the residual proliferative rate of the parental-, Nurr1- and mock-C17.2 control clones. % BrdU+ indicates the percentage of cells which incorporated BrdU after a six-hour pulse in serum free media.

FIG. 1b shows that expression of Nurr1 significantly increases neuronal fate in serum free media. % TuJ1+% BrdU− indicates the percentage of cells which expressed β-tubulin III but did not incorporate BrdU.

FIG. 1c shows that co-culturing two of the clones with E16 ventral mesencephalic cells significantly increases dopaminergic fate. % TH+ indicates the percentage of tyrosine hydroxylase positive C17.2 cells.

FIG. 2a shows the effects of SR11237, bFGF, and EGF on dopaminergic induction. % TH+ indicates the percentage of C17.2 cells in co-culture expressing tyrosine hydroxylase. (C) co-cultures of E16 VM cells with parental C17.2 cells or with Nurr1-C7.2-clone 42 cells; (SR) co-culture plus SR11237; (F) co-culture plus bFGF; (αF) co-culture plus blocking antibody to bFGF (E) co-culture plus EGF.

FIG. 2b demonstrates the link between proliferation and dopaminergic induction. % TH+ indicates the percentage of C17.2 cells after co-culture for 9 DIV expressing tyrosine hydroxylase. % BrdU+ indicates the percentage of those cells which incorporated BrdU.

DETAILED DESCRIPTION

Methods

Nurr1-Over-Expressing Cell Lines

Figure 1:
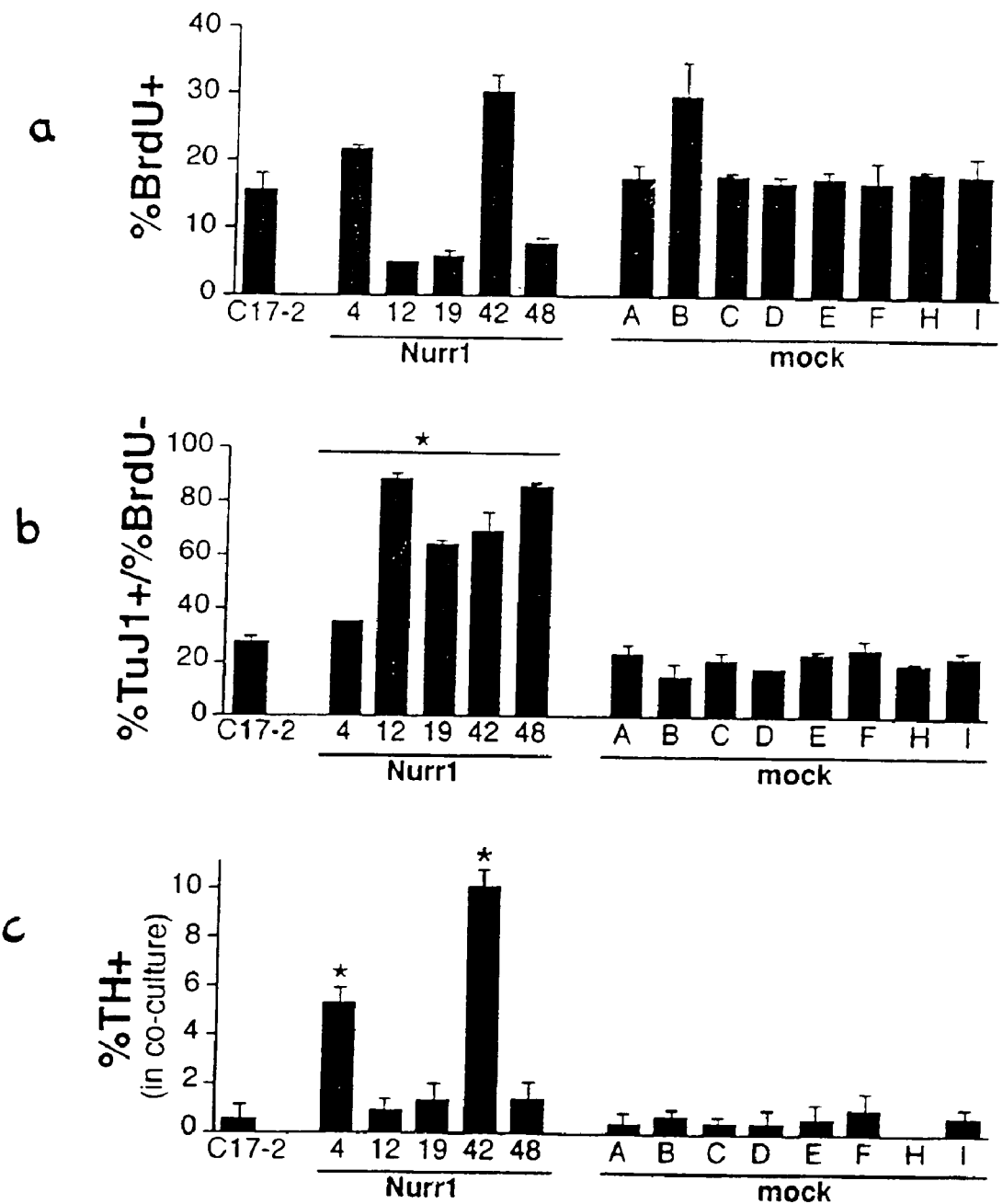
FIG. 1 demonstrates the characterization of the Nurr1-C17.2 clones.

C17.2 cells were cotransfected with a CMX-Nurr1 expression vector (Perlmann, T. et al. Genes Dev. 9, 769-782 (1995)) and PGK-puromycin resistance plasmids (Nurr1 clones) or a PGK-puromycin alone (mock clones). For reporter assays, C17.2 parental cells were transfected with the Nurr1 expression vector, the reporter plasmid (NGFIB-binding response element (NBRE) triplet upstream of TK minimal promoter fused to firefly luciferase) and a pRSV-alkaline phosphatase plasmid at a 2:1:2 ratio.

Fifty Nurr1 transfected clones were selected for puromycin resistance, isolated, amplified and Nurr1 mRNA expression was analyzed by RNase protection assay (RPA). Assays were performed using the RPAII Ribonuclease Protection Assay Kit (Ambion), following the manufacturers, recommendations. A 288 bp antisense Nurr1 cRNA probe spanning nucleotides 1798-2086 of the mouse Nurr1 cDNA sequence (Law, S. W. et al. Mol. Endocrinol. 6, 2129-2135 (1992)) was transcribed with T7 (from a Nurr1 cDNA cloned into the EcoRI/XhoI site of the PBS-KS+ vector, linearised with EcoRI) and labeled with ($\alpha$-32P) CTP (Amersham). Protected cRNA fragments were separated on 4% PAGE under denaturing conditions. The intensity of the signal was analyzed with a phosphoimager MD storm 840 and Nurr1 signal was standardized to the content of GAPDH in every sample.

Cell Culture and Treatments

C17.2 neural stem cells (Snyder, E. Y. et al. Cell 68, 33-51 (1992)) were maintained and passaged as previously described (Snyder, E. Y. et al. Cell 68, 33-51 (1992)). Ventral mesencephala from E16 rat embryos were dissected, mechanically dissociated and plated at a final density of $1\times10^5$ cells/cm$^2$ on poly-D-lysine coated culture wells in a defined, serum-free medium (N$^2$, consisting of a 1:1 mixture of F12 and DMEM containing insulin (10 ng/ml), transferrin (100 μg/ml), putrescine (100 μM), progesterone (20 nM), selenium (30 nM) glucose (6 mg/ml), and bovine serum albumin (1 mg/ml)). After 24 hours in vitro, co-cultures were initiated by directly plating $2.5-5\times10^4$ C17.2-derived cells into the primary cultures; all ages of cultures given use this point as 0 DIV. This sequence of plating and ratio of primary/C17.2 cells resulted in the healthiest cultures, although varying the numbers of C17.2 cells over a 10-fold range did not significantly affect the proportion of TH+ cells observed. Purified Type 1 astrocytes were obtained from mixed glial cultures derived from various regions of P1 rats according to a standard protocol (McCarthy, K. D. et al. J. Cell Biol. 85, 890-902 (1980)). After replating into 6- or 12-well plates, astrocytes were grown to confluency in serum-containing media and changed to N2 medium. After 3-5 DIV, co-cultures were initiated in fresh N2 as described above. All factors were added once, at the initiation of co-culture (concentrations are noted in the Results and Discussion), with the exception of 5-bromodeoxyuridine (BrdU), which was added 4-6 hours prior to fixation. Cultures were maintained in a humidified 5% CO$_2$, 95% air incubator at 37 C and fixed after given time periods with 4% paraformaldehyde for 45 minutes for immunocytochemical analysis.

Immunocytochemical Analysis and HPLC

Fixed cultures were incubated with one of the following antibodies, diluted appropriately in phosphate-buffered saline (PBS) containing 1% bovine serum albumin and 0.3% Triton-X 100: mouse anti-BrdU, 1:50 (DAKO, Denmark), mouse anti-β-tubulin, Type III (TuJ1), 1:250 (Sigma), mouse anti-TH, 1:1000 (Incstar, USA), rabbit anti-β-galactosidase, 1:250 (Cappel, USA) rabbit anti-GFAP, 1:500 (DAKO, Denmark), rabbit anti-AHD-2, 1:4000. Incubations were carried out at 4° C. overnight, or at room temperature for 1 hour. Both processes yielded similar results. After washing, cultures were incubated for 1-3 hr with appropriate secondary antibodies (biotinylated horse-anti-mouse IgG or goat-anti-rabbit IgG, Vector, USA), 1:100, in the same dilution buffer. Immunostaining was visualized with the Vector Laboratory ABC immunoperoxidase kit, using either AEC (red) or SG (grey) substrates. Fluorescent double-labeling of β-galactosidase (i-gal) was performed by substituting the biotinylated secondary with FITC-conjugated antibody (Vector, USA), 1:100. Quantitative immunocytochemical data represent means and standard errors from 100-500 cells counted in each of 3-6 separate wells from 2-4 experiments. For quantitation of TH expression in co-cultures of primary and C-17.2-derived cells, TH was visualized with the brightfield AEC substrate, while β-gal was assessed using FITC, thus all data expressed as "% TH+" represents the number of TH+/β-gal+ divided by total β-gal positive cells.

For analysis of dopamine release, large (10 cm) co-cultures containing approximately 1 million Nurr1-C17.2-c42 or C17.2 parental cells with P1 VM T1A were treated with 200 μl of 50 mM KCl in PBS/0.1 M sodium citrate for 5 minutes while swirling. The supernatants were immediately assayed for dopamine content using high-pressure liquid chromatography (HPLC). Samples were separated with a reverse-phase C-18 column, eluted with acetonitrile and detected electrochemically. Results were verified with a standard containing dopamine, DOPAC, 5-HT, and 5-HIAA.

Long-Term Cultures and Transplantation

Parental C17.2 cells or C17.2-Nurr1-c42 cells were grown in large (locm) insert cocultures with VM type 1 astrocytes for 8 days in the presence of bFGF (10 ng/ml) and SR11237 (1 μM). Cells were then trypsinized off of the insert, pelleted, and resuspended, at a concentration of 100,000 cells/μl, in their own conditioned media; an aliquot of this mixture was then plated into a poly-D-lysine treated 6-well tissue culture plate containing N2 media, while the remainder was used for transplantation. Adult (25-30 grams) CD1 mice housed and treated according to the guidelines of the European Community (86/609/EEC) were anaesthetized with pentobarbital (60 mg/kg i.p.). 25,000 cells were stereotaxically injected into the striatum, at each of the two following coordinates (in mm): AP (bregma)=0.56, L=1.9, DV(dura)=−2.55 and −2.75, with the incisor bar at −3. Twelve days after grafting, mice were transcardially perfused with 4% paraformaldehyde. Brains were postfixed for 2 hours, embedded in 10% sucrose for more than 1 day and frozen in dry-ice cooled isopentane. 14 micron cryostat sections were processed for TH immunohistochemistry using mouse anti-TH (Incstar, Minnesota, USA) 1:1000, and donkey anti-mouse rhodamine (Jackson, Pennsylvania, USA) 1:100 antibodies. TH-positive cells were photographed using a Hamamatsu camera attached to a Zeiss Axioplan 2 microscope.

Results and Discussion

Expression of Nurr1 Above Basal Levels in Multipotent Neural Stem Cells

The inventors used a well characterized clone of multipotent neural stem cells termed C17.2 (Snyder, E. Y. et al. Cell 68, 33-51 (1992)). Initially derived from developing mouse cerebellum, C17.2 cells have been immortalized with v-myc, contain a lacZ reporter, possess the ability to differentiate into neurons, astrocytes, and oligodendrocytes in vitro and in vivo, and upon transplantation into the developing brain, adopt regionally-appropriate neuronal phenotypes (Snyder, E. Y. et al. Cell 68, 33-51 (1992); Snyder, E. Y. et al. Nature 374, 367-370 (1995)). Moreover, the same single factors known to direct the differentiation of primary stem cells from the fetal and adult central nervous system (Johe, K. K. et al. Genes Dev. 10, 3129-3140 (1996)) direct the differentiation of C17.2 cells in vitro.

C17.2 cells were stably transfected as described below and fifty Nurr1 clones were analyzed for transgene expression by RNase protection assay (RPA). Several Nurr1 clones overexpressed the transgene, of which the five highest expressors were selected for analysis. These five selected clones expressed much higher levels of Nurr1 than parental C17.2 cells, or cells of the ventral mesencephalon, cerebellum or cortex. 8 randomly chosen, mock control clones were also selected. All Nurr1 clones behaved similarly to the parental and mock clones in serum-containing media, with no obvious differences in growth rate or morphology.

Differentiative Capacity of Nurr1 Over-Expressing Clones

To define the differentiative capacity and phenotypic fate of Nurr1 over-expressing clones, the inventors examined the behavior of the clones after low density passage into serum-free, defined media (conditions which allow for differentiation). In this condition, the parental cell line begins to differentiate, so that after 4-5 days in vitro (DIV), 80-85% of the population is post-mitotic (i.e. BrdU negative after extended pulse), while approximately 20-30% of the post-mitotic cells adopt a neuronal fate, judged by expression of β-tubulin III (TuJ1).

The effects of Nurr1 on differentiative capacity, as measured by incorporation of 10 µM BrdU after a 6 hour pulse in serum-free media, were varied. Although there was a trend toward increased differentiation within the Nurr1 clones, no clear effect of the transgene on this process was seen (FIG. 1A) However, the effects of Nurr1 on the fate of post-mitotic cells were clear and robust (FIG. 1B). Expression of the Nurr1 transgene significantly increased neuronal fate in serum-free media, as judged by expression of β-tubulin III (TuJ1), to an average of 68% of the post-mitotic cells across all five clones (global effect of Nurr1 transgene vs. mock, *P<0.0001 by 2-way ANOVA). In four of five Nurr1 clones, the vast majority of post-mitotic cells (greater than 60%) adopted a neuronal fate, a phenomenon not seen in any of the mock clones.

Although Nurr1 appears to restrict the C17.2 cell line to neuronal lineages, the neurochemical fate of these neurons was not dopaminergic as no significant tyrosine hydroxylase (TH, a marker for dopaminergic neurons) immunoreactivity was detected in any of the Nurr1 clones under these conditions.

Induction of Nurr1 Over-Expressing Clones to the Dopaminergic Fate

The inventors treated the Nurr1 clones with a variety of trophic factors, mitogens, cytokines and other agents known to be important in the proliferation (basic fibroblast growth factor (bFGF), epidermal growth factor (EGF), insulin-like growth factor, fetal calf serum), differentiation (retinoic acid, dopamine, forskolin, sonic hedgehog) and survival (glial cell line-derived neurotrophic factor, brain-derived neurotrophic factor, neurotrophin-3, ciliary neurotrophic factor) of endogenous dopaminergic neurons. None of these factors induced TH expression in any of the clones, alone or combined.

The Nurr1 clones were co-cultured in vitro with primary cultures derived from E16 rat ventral mesencephalon, the age and region where endogenous dopaminergic neurons of the substantia nigra have just been born (Altman, J. et al. Neurogenesis and Neuronal Migration, in The Rat Nervous System, 2nd edition (ed. Paxinos, G. Academic Press, San Diego) p. 1054 (1995)). Under these conditions a significant percentage of cells from two of the Nurr1 lines (the clones with the highest proliferative capacity, clones 4 and 42) demonstrated measurable amounts of TH immunoreactivity (FIG. 1C—*P<0.0001, interaction of transgene vs. clone by 2-way ANOVA). Little or no TH staining was seen in the C17.2 parent or any of the mock control lines. Phase-contrast microscopy of the cocultures revealed large proliferative clusters of Nurr1-clone-derived TH+ cells.

Collectively, these observations suggested that one or more local factors derived from the primary cultures interacted directly or indirectly with Nurr1 to induce TH expressing neurons. TH expression was limited to a minority subpopulation within a fraction of the Nurr1 clones.

Treatment of Co-Cultures with SR11237, bFGF and EGF

Figure 2:
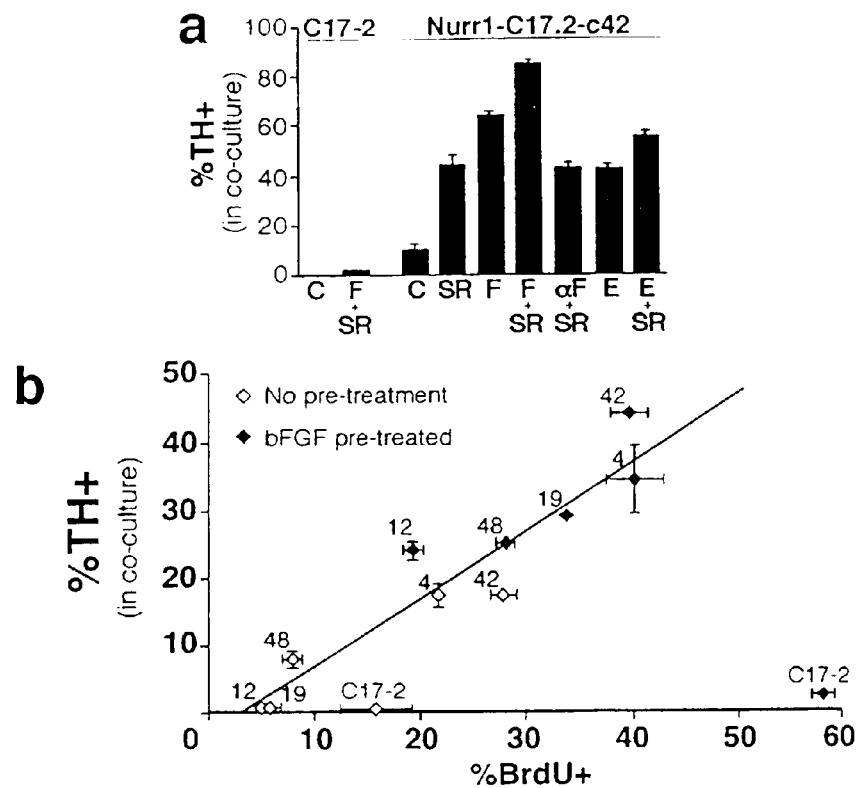
FIG. 2 demonstrates the role of retinoids, bFGF, and proliferation in the induction of dopaminergic neurons from Nurr1-over-expressing neural stem or progenitor cell lines in ventral mesencephalic co-cultures.

Treating co-cultures of the highest TH-expressing Nurr1 clone (clone 42) and primary VM cells with combinations of the previously mentioned factors was generally ineffective in increasing TH expression, with three important exceptions: the synthetic retinoid analog SR11237, bFGF, and EGF (FIG. 2A).

Addition of SR11237 (to 1 µM) and bFGF (to 10 ng/ml) to the parental C17.2 cells in co-culture did not induce expression of TH, however, each of these molecules induced TH expression in 40-60% of the Nurr1-C17.2 clone 42 population when added to co-cultures in serum free media. The effects of bFGF could be substituted by EGF. Moreover, the effects of SR11237 and bFGF or EGF were additive at saturating doses (up to 90% LacZ+ were TH+) suggesting that they may act through distinct mechanisms.

SR11237 specifically stimulates RXR retinoid receptors (Lehmann, J. M. et al. Science 258, 1944-1946 (1992)) which have been shown to heterodimerize with Nurr1 to form transcription-initiating complexes (Perlmann, T. et al. Genes Dev. 9, 769-782 (1995)). This observation, along with observations that all-trans retinoic acid was without effect, suggest that a functional interaction between Nurr1, RXR receptors and primary VM cells may be involved.

Retinoids and FGF have previously been shown to play a role in normal dopaminergic neuronal development (Ye, W. et al. Cell 93, 755-766 (1998); Eichele, G. Trends Genet. 13, 343-345 (1997); Krezel, W. Science 279, 864-867 (1998)). However, although these factors increase the proportion of TH expressing cells as discussed above, the inventors have shown that the effects of these factors on Nurr1-C17.2-c42 (c42) seem to be modulatory. Antagonism of either, with blocking antibodies or with specific RAR or RXR antagonists, did not prevent basal TH expression of c42 in co-culture (i.e. about 10%, FIG. 1C). Antagonism of sonic hedgehog using blocking antibodies was also ineffective in preventing basal TH expression. Thus, the only obligate requirement for the induction of a dopaminergic phenotype in c42 seems to be exposure to signals derived from primary ventral mesencephalic cells.

Pretreatment of Clones with bFGF and EGF bFGF and EGF are both directly mitogenic to the C17.2 cells (Kitchens, D. L. et al. J. Neurobiol 25 (7), 797-807 (1994)), but it was found that after extended treatment with either factor in serum-free medium (SFM), the baseline proliferation of most clonal lines remained unexpectedly elevated after passage into SFM alone. Moreover, it was surprising that Nurr1 clones with the highest amount of residual proliferation in serum free medium (clones 4 and 42), demonstrated significant TH expression in co-culture.

The inventors reasoned that increasing the proliferation of other Nurr1 clones should increase the number of TH expressing neurons. Nurr1 clones were pretreated with bFGF for 5 DIV prior to splitting and replating into primary ventral mesencephalic cultures. Sister cultures were assayed for both proliferation after pretreatment and TH expression after co-culture for 9 DIV. This procedure enabled selective examination of the effects of bFGF on the Nurr1 clones and eliminated the mitogenic effects of bFGF on primary cells as well as its indirect trophic effect on primary dopaminergic neurons.

BrdU labeling of bFGF-pretreated Nurr1 clones was increased at 24 hours after passage of cells into co-culture, as compared with cells directly split out of serum-containing medium (rightward shift of individual clones on X-axis, FIG. 2B). Concomitant with this increase in proliferation, proportional increases in the percentage of TH-positive cells were observed in all of the Nurr1 clones (upward shift of clones on Y-axis, FIG. 2B), reaching as high as 45% TH+ (clone 42). In fact, regression analysis indicates a significant linear relationship ($r^2$=0.890 by regression) between the proliferative capacity of the Nurr1 over-expressing clones at the initiation of co-culture and the propensity to express TH after differentiation within, as well as between, individual clones after 9 DIV.

The above results therefore suggest that Nurr1 over-expressing clones should preferably be mitotic when first brought into contact with primary VM cells, or with one or more factors supplied by or derived from primary VM cells, i.e. that an important influence on differentiation to a dopaminergic fate in Nurr1 clones is their proliferative capacity.

Further support is provided by the observation that, at the time when most TH-expressing c42 cells begin appearing in co-culture (6 DIV), nearly all of them are still mitotic (BrdU positive after acute pulsing at 6 DIV. However, after similar treatment of co-cultures at 9 DIV, the vast majority of TH+ cells are BrdU negative, suggesting withdrawal from the cell cycle following induction of measurable TH expression.

Previous studies examining the adoption of phenotypic fate during cerebral cortical (McConnell, S. K. et al. Science 254, 282-285 (1991)) and spinal cord (Ericson, J. et al. Cell 87, 661-673 (1996)) development have demonstrated that exposure of non-committed neuroblasts to spatially-restricted, local factors induces specific phenotypes within these populations, but this induction is contingent upon continuous exposure up to and including the terminal S-phase of the neuroblast. A similar mechanism may underlie the present observations.

Analysis of the Inductive Signal from Primary Ventral Mesencephalic Cells

Primary ventral mesencephalic cultures typically contain a mixture of dopaminergic and other neurons, astrocytes, oligodendrocytes, as well as assorted non-neural elements such as microglia, endothelial cells, and fibroblasts. To identify the source of the TH-promoting activity, the inventors performed a crude separation of the primary cells based on adhesion; the rapidly adherent population was enriched for glial and non-neural elements, while the non-adherent population consisted mainly of neurons, oligodendrocyte precursors, and a few astrocytes.

Figure 3:
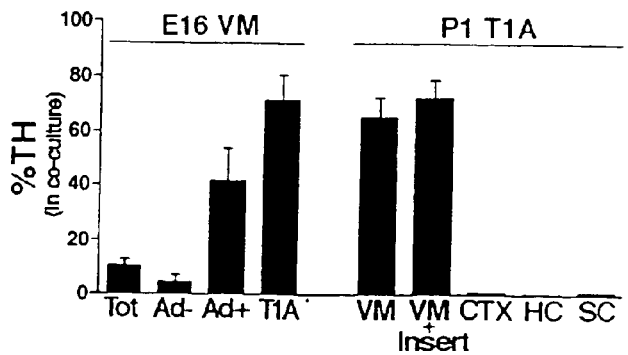
FIG. 3 shows that VM Type 1 astrocytes induce a dopaminergic phenotype on a Nurr1 over-expressing neural stem cell line (Nurr1-C17.2-clone 42). % TH+ indicates the percentage of clone 42 cells expressing tyrosine hydroxylase. (E16 VM) co-culture of clone 42 with E16 ventral mesencephalon cells; (Tot) co-culture with total primary cells; (Ad+) co-culture with adherent cell fraction; (Ad−) co-culture with non-adherent cell fraction; (T1A) co-culture with Type 1 astrocytes; (P1 T1A) co-culture with Postnatal day 1 Type 1 astrocytes from the ventral mesencephalon. (Insert) insert separates clone 42 cells from P1 T1A cells in co-culture; (CTX) co-culture with cortex, (HC) co-culture with hippocampus; (SC) co-culture with spinal cord.

Co-culture of these fractions with c42 demonstrated that the majority of TH-inducing activity was contained within the rapidly adherent population of E16 ventral mesencephalon cells (FIG. 3). The inventors then prepared purified cultures of Type 1 astrocytes from E16 ventral mesencephalon and demonstrated that T1A were the source of TH-inducing activity: in the absence of any added factor, the number dopaminergic cells derived from the Nurr1-c42 line dramatically increased. Furthermore, this activity was not restricted to early development, as astrocytes isolated from the VM of newborn rats induced equivalent numbers of TH positive c42 cells (about 70%) (FIG. 3).

Nurr1-C17.2-c42 cells were treated with Type 1 astrocyte conditioned media or membrane fragments, respectively. However, neither of these treatments induced a significant increase in the number of TH expressing cells, suggesting that this inducing activity was highly labile. The inventors co-cultured astrocytes and Nurr1-C17.2-c42 cells, but spatially separated the two populations (by about 1 mm) via a microporous insert (0.4 µm porous membrane). The insert allowed free passage of macromolecules but prevented contact between the two populations. In this environment, TH expression was induced in Nurr1-C17.2-c42 cells at a level equivalent to direct co-culture (FIG. 3). These results provide indication that ventral mesencephalic Type 1 astrocytes secrete a highly labile diffusible factor which interacts with Nurr1 over-expressing lines to induce TH expression.

Inductive Activity of T1A from Other Brain Regions

The inventors then examined whether the inductive activity is restricted to Type 1 astrocytes from the ventral mesencephalon. T1A were isolated from several brain regions which contain populations of Nurr1-expressing cells during development (Zetterström, R. H. et al. Mol. Brain. Res. 41, 111-120 (1996)). No increase in the number of TH immunoreactive cells was observed in c42, compared to parental C17.2 cells, when co-cultured with T1A from other brain regions including cerebrocortex, hippocampus, or spinal cord (FIG. 3). This indicates that a putative TH-inducing factor is specifically and selectively produced by ventral mesencephalic Type 1 astrocytes.

However, c42 cells were not unaffected by astrocytes from these regions. Cells of this line developed distinct, neuronal-like morphologies unique to each region. Under the same conditions however, the C17.2 parental line tended to display a uniform mixture of polygonal, bi- and tripolar morphologies. Collectively, these data suggest that astrocytes from distinct brain regions secrete unique, or unique combinations of, factors which interact with Nurr1-expressing cells to produce specific, and perhaps regionally appropriate, neuronal phenotypes. Confirmation is obtained by identifying the neuronal phenotypes which are produced in the co-cultures. Specific neuronal markers are used, such as NPY, substance P, Ach, and Islet 1. Further support is obtained by grafting C17.2 cells expressing Nurr1 above basal levels intracerebro-ventricularly at early embryonic stages to allow for their integration. The neuronal phenotypes originated by these cells are determined by lacZ expression and immunohistochemistry against a specific neuronal marker.

The Mechanism of Dopaminergic Induction

Figure 5:
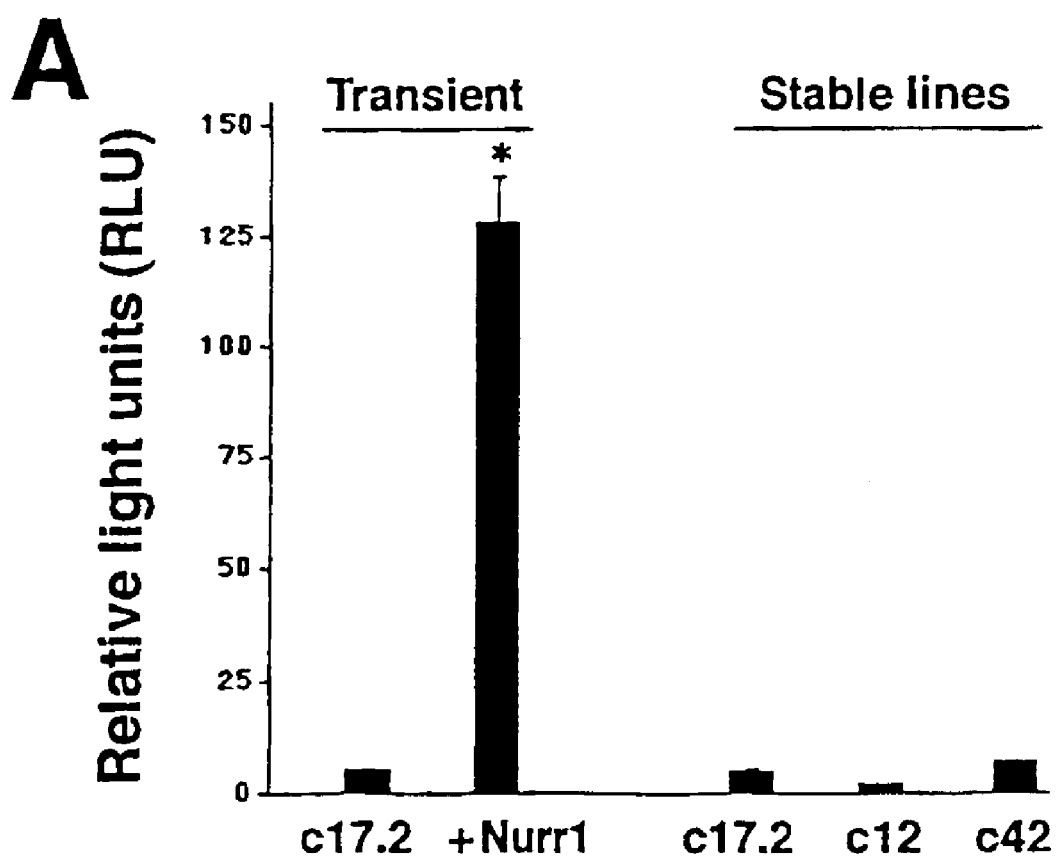
FIG. 5 shows that early activity of Nurr1 produces long-lasting changes in gene expression in C17.2 cells. Relative light units (RLU) indicates the expression of luciferase from a Nurr1 activated NBRE-luciferase reporter.

The inventors compared Nurr1 activity in C17.2 cells shortly after transfection with Nurr1 activity in established C17.2-Nurr1 clones. They found that significant Nurr1 transactivational activity was detected 36 hours after cotransfection of the Nurr1 expression vector and a Nurr1-responsive NBRE-luciferase reporter into C17.2 cells. No significant increase in basal Nurr1 transactivational activity was observed after transfection of the reporter into stable, proliferating C17.2-Nurr1 clones (grown in serum) (FIG. 5), or after transfection into differentiated clones obtained after passage into serum free medium.

These data indicate that Nurr1 is not active during the neuronal differentiation of stable C17.2-Nurr1 clones, and suggest that earlier transient high levels of Nurr1 activity may have conferred upon the Nurr1 clones long-lasting competence to be dopaminergic.

Changes in Gene Expression in Nurr1 Clones

The inventors examined changes in gene expression in Nurr1 clones. GFR α1 and GFR α2 mRNA levels in mock and Nurr1 clones were examined using RNase protection assays (GDNF familiy receptor al; GDNF refers to Glial cell line-Derived Neurotropic Factor). C17.2 and all the mock clones examined expressed high levels of GFR α1 mRNA and very low levels of the related receptor GFR α2. In contrast, all Nurr1 clones demonstrated the inverse profile, i.e. very low GFR α1 and very high GFR α2 mRNA levels, suggesting that in C17.2 cells Nurr1 does not directly induce the TH+ phenotype, but rather acts indirectly, by producing stable up- or down-regulation of relevant proteins. In such a way, Nurr1 may bestow multipotent cells with the competence to respond to specific factors, including those derived from ventral mesencephalic astrocytes.

The effects of Nurr1 activity on the pattern of gene expression is further investigated by analysing the expression of genes important for the specification of midbrain neurons and ventral phenotypes (e.g. Shh, Patch, Smo, Gli genes, Hes, FGF8, Ptx3, Pax genes, Engrailed 1 and 2) and genes important for neurogenesis and differentiation (e.g. Noggin, Chordin, Follistatin, Mash1, Math1, NeuroD, Neurogeninl-3, Notch1-3, Delta, Serrate and Myt1).

The Dopaminergic Phenotype

Figure 4:
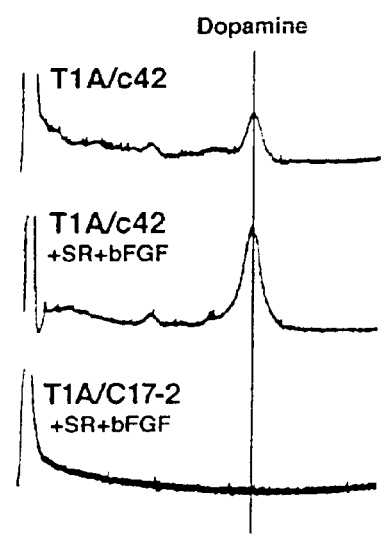
FIG. 4 illustrates HPLC analysis of supernatants collected from co-cultures of Type 1 astrocytes of the ventral mesencephalon (T1A) with either KCl-depolarized Nurr1-C17.2-clone42 (c42) cells, or KCl depolarized parental C17.2 (C17-2) cells. (+SR+bFGF) co-cultures plus of bFGF and SR11237.

The gain of TH expression represented the adoption of a legitimate dopaminergic phenotype within the Nurr1-C17.2-c42 line. By convention, the ability to release dopamine in response to membrane depolarization is the vital criterion for designation of neurochemical phenotype as dopaminergic. Co-cultures of parental or c42 lines and VM astrocytes were thus treated acutely with 50 mM KCl and the supernatants were assayed for monoamine content with HPLC. Significant release of dopamine and its metabolite DOPAC was detected in co-cultures containing c42, with increased release detected in co-cultures treated with factors enhancing dopaminergic differentiation, e.g. SR11237 and bFGF, thereby correlating dopamine release to the number of TH expressing cells (FIG. 4). No dopamine release was observed in the parental line. Thus, TH expressing Nurr1-C17.2-c42 cells may be considered truly dopaminergic.

The TH expressing Nurr1-C17.2-c42 line was of a ventral mesencephalic dopaminergic type. Nurr1-C17.2-c42 cells in co-culture acquired immunoreactivity for aldehyde dehydrogenase-2 (AHD-2; FIG. 4), an enzyme selectively expressed in developing dopaminergic precursors within the ventral mesencephalon (McCaffery, P. et al. Proc. Natl. Acad. Sci. USA 91, 7772-7776 (1994)). They also expressed c-ret mRNA, the signaling receptor for GDNF (Trupp, M. et al. Nature 381, 785-789 (1996); Jing, S. Q. et al. Cell 85, 1113-1124 (1996)) which is present in dopaminergic neurons (Trupp, M. et al. Nature 381, 785-789 (1996)). Furthermore, TH positive c42 cells demonstrated similar responses to factors with known neurotrophic effects on dopaminergic progenitors (Studer, L. et al. Nature Neurosci. 1, 290-295 (1998)) and primary ventral mesencephalic dopaminergic neurons in vitro (Hyman, C. et al. J. Neurosci. 14, 335-347 (1994); Lin, L. H. et al. Science 260, 1130-1173 (1993)) (FIG. 4). Co-cultures were first treated with SR11237 and bFGF to induce a dopaminergic phenotype, after which the media was changed to N2 with or without various growth factors. At 9 DIV bFGF and neurotrophin-3 (NT-3 30 ng/ml) dramatically increased the number of TH+ cells in the culture, compared to the N2 control condition; Brain Derived Neurotrophic Factor (BDNF, 30 ng/ml), Ciliary Neurotrophic Factor (CNTF, 10 ng/ml) and Glial cell line-Derived Neurotrophic Factor (GDNF, 10 ng/ml) induced neuritogenesis and/or hypertrophy on Nurr1-c42-derived dopaminergic neurons. Thus the behavior of TH expressing c42 cells parallels that of endogenous neurons of the substantia nigra, so these cells are ventral mesencephalic-like dopaminergic neurons.

Stability of Induced Dopaminergic Neurons

The inventors assessed the long term stability of the induced dopaminergic phenotype in vi tro and in vivo, particularly after removal of astrocyte-derived inductive factors. c42 cells were co-cultured in inserts with VM type 1 astrocytes for 8 days, removed from the inserts and replated into defined N2 media without additional factors for 14 days. Although some cellular attrition was observed in the two weeks after removal from co-culture, a significant number of cells displayed a highly mature dopaminergic phenotype, including long elaborate processes, hypertrophic cell bodies and intense levels of TH-immunoreactivity.

c42 cells from parallel co-cultures were also surgically injected into adult mouse corpus striatum and allowed to mature for 12 days, in the absence of any additional tropic factors or supportive cells (i.e. astrocytes, oligodendrocytes, or other neurons). Although cells were lost in this condition, a small but significant number of c42 derived dopaminergic cells displayed a high level of differentiation and apparent integration into the host tissue. No TH+ cells derived from the c17.2 parental line were found in either of the long term in vitro or in vivo experiments. Thus the observation that some c42 cells maintained or even increased TH expression after removal from Type 1-derived factors shows that, after dopaminergic induction, their phenotype is stable. Since only a limited number of surviving TH+ cells could be detected, exogenously applied tropic factors or supporting cells are required for long-term survival.

Treatment of Neurodegenerative Disease

Confirmation of the ability of c17.2 derived neurons to treat neurodegenerative disease is obtained using an in vivo model of Parkinson's disease. The false neurotransmitters 6-hydroxydopamine (6-OHDA) or MPTP are specifically taken up by neurons and lead to oxidative stress and loss of dopaminergic and noradrenergic neurons.

Nurr1-c17.2 cells that have been differentiated into dopaminergic neurons in vitro are surgically implanted into either the substantia nigra or the striatum of 6-OHDA treated mice. The ability of these cells to integrate and fully differentiate is morphologically evaluated by β-gal staining, TH-immunohistochemistry and in situ hybridisation for dopamine transporter and dopamine receptors.

The ability of undifferentiated Nurr1-c17.2 cells to spontaneously differentiate in vivo toward the dopaminergic phenotype is assessed by intrastriatal or intranigral grafting of such cells into 6-OHDA treated animals. The dopaminerigc phenotype is detected as described above.

The ability of Nurr1-c17.2 cells grafted into the striatum or substantia nigra to rescue motor asymmetries induced by unilateral 6-OHDA treatment is confirmed by assessment of circling behaviour in apomorphine and amphetamine tests (Schwarting, R. K., et al., (1996) Progress in Neurobiology, 50(2-3), 275-331).

SUMMARY

In conclusion, the results presented herein demonstrate that expression of Nurr1 above basal levels in neural stem or progenitor cells induces a neuronal fate. Moreover, Type 1 astrocytes of the ventral mesencephalon, but not from other brain regions, release one or more soluble factors which induce neural stem or progenitor cells originally obtained from a non-dopaminergic brain region and which express Nurr1 above basal levels, to develop into dopaminergic neurons of the ventral mesencephalon. Thus dopaminergic neurons can be generated from neural stem or progenitor cells through a process including expression of Nurr1 above basal levels in the cells and contact of the cells with one or more factors supplied by or derived from type 1 astrocytes of the ventral mesencephalon. In addition, the results suggest that primary astrocytes may be the source of signals required for the induction of regionally appropriate neuronal phenotypes in multiple brain structures.

The methods described herein, which take advantage of the multipotential capacity of neural stem or progenitor cells, selector genes such as Nurr1, and primary astrocytes, provide for the production of neurons of a desired neurochemical phenotype as a source material for neuronal transplantation in the treatment of neurodegenerative diseases. The induction of midbrain dopaminergic neurons may be used in a cell replacement strategy to treat Parkinson's disease.

The invention claimed is:

1. A method of inducing a dopaminergic neuronal fate in a neural stem cell or neural progenitor cell comprising:
    (a) incubating in vitro a neural stem cell or a neural progenitor cell that overexpresses Nurr-1, wherein Nurr-1 in the cell is overexpressed when compared to an unmodified neural stem cell or neural progenitor cell in vitro under non-pathological conditions, and
    (b) co-culturing the cell with a Type 1 astrocyte of the ventral mesencepahlon, thereby contacting the cell with one or more factors secreted from said Type 1 astrocyte, whereby the cell that overexpresses Nurr1 is induced to a dopaminergic neuronal fate.

2. The method according to claim 1 comprising additionally contacting the cell with fibroblast growth factor 8 (FGF8).

3. The method according to claim 1 comprising transforming a neural stem cell or a neural progenitor cell with a DNA sequence encoding Nurr1 operatively linked to a promoter.

4. A method according to claim 1 wherein the Type 1 astrocyte is immortalized or is of an astrocyte cell line.

5. A method according to claim 1 wherein said cell is mitotic when it is contacted with said one or more factors.

6. A method according to claim 1 wherein said cell is additionally contacted with one or more agents selected from the group consisting of: basic fibroblast growth factor (bFGF) epidermal growth factor (EGF), an activator of the retinoid X receptor (RXR), and 9-cis retinol.

7. A method according to claim 1 wherein said cell is additionally contacted with a member of the fibroblast growth factor (FGF) family of growth factors.

8. A method according to claim 7 wherein said cell is contacted with bFGF or EGF, and SR11237.

9. A method according to claim 1 wherein the neural stem cell or neural progenitor cell is pretreated with bFGF and/or EGF prior to contacting the cell with one or more factors secreted from a Type 1 astrocyte of the ventral mesencephalon.

10. A method according to claim 1 further comprising formulating a dopaminergic neuron produced by the method into a composition comprising one or more additional components.

11. A method according to claim 10 wherein the composition comprises a pharmaceutically acceptable excipient.

12. The method of claim 1 whereby 5% to 70% of the cells that overexpress Nurr 1 are induced to a dopaminergic neuronal fate.

* * * * *